(12) United States Patent
Clopton et al.

(10) Patent No.: US 7,340,308 B1
(45) Date of Patent: Mar. 4, 2008

(54) METHOD FOR ELECTRICALLY STIMULATING THE COCHLEA

(75) Inventors: Ben M. Clopton, Bainbridge Island, WA (US); Matthew D. Carson, Snoqualmie, WA (US); Timothy J. Johnson, Kent, WA (US)

(73) Assignee: Advanced Cochlear Systems, Inc., Snoqualmie, WA (US)

( * ) Notice: Subject to any disclaimer, the term of this patent is extended or adjusted under 35 U.S.C. 154(b) by 324 days.

(21) Appl. No.: 11/148,576

(22) Filed: Jun. 8, 2005

Related U.S. Application Data

(60) Provisional application No. 60/578,178, filed on Jun. 8, 2004.

(51) Int. Cl.
*A61N 1/36* (2006.01)

(52) U.S. Cl. .......................................... 607/57

(58) Field of Classification Search ............ 607/55–57
See application file for complete search history.

(56) References Cited

U.S. PATENT DOCUMENTS

| | | | |
|---|---|---|---|
| 5,999,856 A | * | 12/1999 | Kennedy ...................... 607/57 |
| 6,480,820 B1 | | 11/2002 | Clopton et al. ............. 704/203 |
| 2007/0032838 A1 | * | 2/2007 | Seligman ..................... 607/55 |

* cited by examiner

*Primary Examiner*—Kennedy J. Schaetzle
(74) *Attorney, Agent, or Firm*—Timothy E. Siegel

(57) ABSTRACT

A method of stimulating neurons in a patient's cochlea. The method uses a plurality of cochlear electrodes, substantially arranged in a linear array within the cochlea and a relatively distant electrode. Charge is injected through a first one of the cochlear electrodes and an opposite charge is injected on either the relatively distant electrode; or a set of adjacent cochlear electrodes, being adjacent to the first one of the cochlear electrodes; or on a combination of the relatively distant electrode and the set of adjacent electrodes; and choosing the electrode or electrodes on which to inject charge in dependency on sound volume to be represented.

19 Claims, 4 Drawing Sheets

METHOD FOR ELECTRICALLY STIMULATING THE COCHLEA

RELATED APPLICATIONS

This application claims priority from provisional application 60/578,178 filed on Jun. 8, 2004.

BACKGROUND OF THE INVENTION

The stimulation of the cochlea performed by a cochlear implant typically includes the reception of sound by a microphone placed near to a patient's ear and based on the analysis of this sound, the choice of a set of electrical injection contact points to be stimulated along the cochlea, the current levels to be injected at the injection electrical contact points and for each injection contact point a set of current return points and the current levels to be accepted at each one of these points, or alternatively, an opposite polarity voltage level to be placed at each current return contact point. A problem that has been encountered in cochlear stimulation is that of a fairly small dynamic range of stimulation. That is, the loudest sound comfortable to a patient (the "maximum comfort level" or MCL), is not as much greater than the softest sound detectable by the patient (the "threshold intensity") as is the difference between softest sound and loudest sound in a natural hearing person.

U.S. Pat. No. 6,480,820, which is incorporated by reference as if fully set forth herein, discloses a method for recognizing sound events that may then form the basis for a scheme of cochlear stimulation. First a vector comprised of the instantaneous phase and magnitude of a sound signal time sample from one band pass filter, is computed. Then the moments when this vector passes the real axis are determined and the magnitude of the vector at these moments is determined. In the following text, these values are described as $m_t$, the desired strength of stimulation. Other methods, however, may be used to find a set of values, $m_t$.

DETAILED DESCRIPTION OF THE PREFERRED EMBODIMENT

Figure 1A:
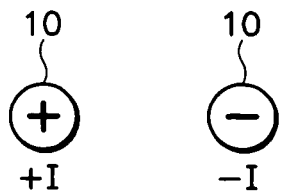
FIG. 1A is an illustration of a dipole contact configuration.

In one preferred embodiment, the present method is a method for electrically stimulating the cochlea, brain tissue or muscle tissue in order to lower the threshold intensity, to restrict the spread of neural excitation and thereby increase channel independence, and to extend the dynamic range of stimulation. The method is predicated on a base of technological developments making the approach feasible with support from a gathering body of empirical observations on the nature of neural population responses to electrical stimulation.

In one preferred embodiment the method makes use of a scalar electrode array positioned near the neurons of the spiral ganglion lying along the tonotopic continuum in the modiolus of the cochlea, in Rosenthal's canal. The array may have adjacent electrode contacts spaced less than 500 µm center-to-center. Currents from these contacts are taken as charge-balanced pulses to minimize contact erosion and cytotoxic byproducts. While the method does not restrict the stimulating waveforms beyond their being charge balanced to meet safety requirements, it may be used to substantially maximize effectiveness in evoking neural responses. Temporally symmetrical, biphasic pulses of a few tens to a few hundreds of microseconds in duration are practical approximations for these pulses. Temporally asymmetrical, but charge-balanced pulses may be used to meet other goals.

The preferred embodiment consists of determining for the frequency and magnitude of sound at each moment, a current delivery scheme through a specified set of contacts with specified intensities and polarities to achieve a desired spatial pattern of neural excitation in the auditory nerves of the cochlea. These contact patterns and intensities are determined from clinical measures of the implant wearer's psychophysical responses. A lookup table of contact patterns and intensities is stored in computer readable media in the cochlear implant system and referenced by the data processor of the system, which may also perform interpolation to find the exact desired pattern and intensity for a particular tone and loudness.

The relevant electrical, neurophysiological, and psychophysical parameters and measurements will be described in the next section. This will be followed by a review of known empirical evidence pertaining to neural responses to spatial contact patterns and intensities. The goals of the method and its implementation will then be detailed.

Relevant Parameters and Measurements

Physics of Electrical Stimulation. The electrical stimulation of tissue is constrained to have current conservation, i.e., the rate of charge sourcing must equal the rate of charge sinking since there are no appreciable capacitive effects. For safety reasons, the time-integrated charge at each contact must be zero (charge balancing). The effectiveness of electrical stimulation in neural and muscle tissue depends on the redistribution of charge across cellular membranes occurring over a few hundred microseconds at most, and this depends on rapidly varying potential gradients across portions of neurons or muscle cells.

In general, the larger the potential gradient across a cell is, the greater the effect on cell-membrane potential and subsequent changes in cell response. Quantitatively this maximizing of gradients near cells is equivalent to maximizing the second spatial derivative of the potential field. Given a fixed three-dimensional electroanatomy of the tissue this maximization is best achieved by placing small electrode contacts near neurons or muscle cells. Both of these conditions increase current density near the cells and, secondarily, potential gradients across the cell bodies as the currents disperse and converge around sources and sinks. Spatial positioning and surface areas of electrode contacts relative to the stimulated tissues thus determine the effects of electrical currents passed between the source and sink ensembles of electrode contacts. The method to be described is a dynamic manipulation of effective electrode-contact patterns, positions, and surface areas to effect optimal neural responses.

Figure 1B:
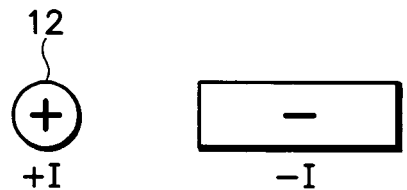
FIG. 1B is an illustration of a monopole contact configuration.
Figure 1C:
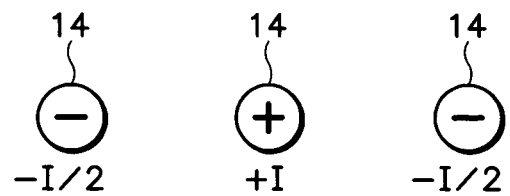
FIG. 1C is an illustration of a tripole contact configuration.

Spatial Contact and Intensity Patterns. FIG. 1 illustrates the terminology commonly used for spatial contact patterns and current intensities. A dipole 10 (FIG. 1A) is an ideal physical concept with two points sourcing and sinking current. In practice "bipolar" stimulation is through two contacts with significant metallic surface areas. Monopoles 12 (FIG. 1B) are small electrode contacts passing current to a distant, much larger "reference" or "extra cochlear" contact. For cochlear stimulation the monopolar contact is in the scala tympani, and the reference contact is external to the cochlea. Because of the large difference in surface areas the current densities and associated potential gradients near the monopole are much greater than near the reference. Another spatial configuration for contacts is the tripole 14 (FIG. 1C). If the tripole has the current values shown (−I/2, +I, −I/2) it can be referred to as a "quadrupole," the additive combination of two dipoles (four contacts) with currents −I/2 and +I/2 from two sources combined in the center.

Note that one contact has been shown positive and one negative in these illustrations, but this relationship reverses when the phase of a biphasic pulse reverses. This is important because neurons near the cathode are more likely to be stimulated, so a temporal sequencing of stimulation may occur near each contact if they have similar surface areas. This is less likely to occur if one has a much larger surface area because it reduces local current densities and potential gradients.

Threshold. The minimum current intensity for evoking a neural response is defined as the threshold stimulus intensity (see FIG. 2). Since increasing current values are associated with undesirable electrochemical processes for metallic electrodes, a requirement of system design and a goal of this method is the minimization of threshold intensities. Monopolar stimulation of the cochlea has been observed to have lower thresholds than multipolar stimulation, an effect predictable from electric field theory. The method is designed to utilize the low-threshold characteristic of monopoles in combination with the advantages of multipolar stimulation to be described.

Figure 2:
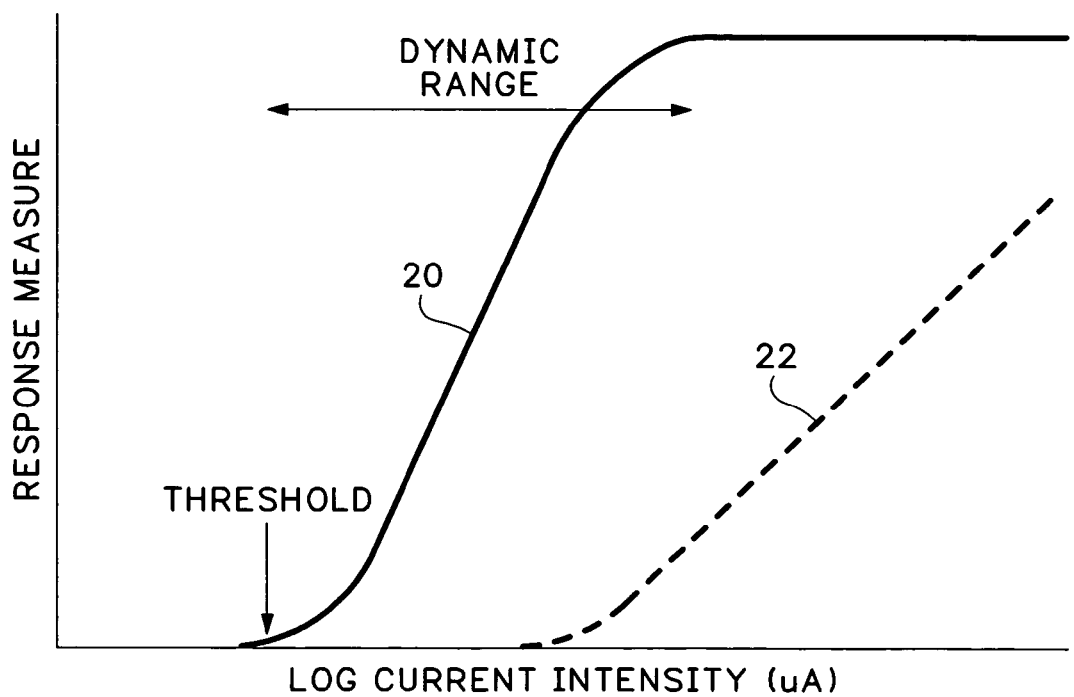
FIG. 2 is a graph showing a comparison of the stimulatory effects of monopole and quadrupole stimulation, versus current.

Dynamic Range. FIG. 2 shows the threshold and dynamic range for a typical response growth curve 20 with monopolar stimulation (curve A). Thresholds are usually 200 to 300 µA or less for monopoles with a rapid rise over a 4 to 6 decibels (dB) dynamic range to a level of response saturation. As suggested in the dashed curve 22, bipolar stimulation usually has threshold values about 6 dB above monopoles with quadrupolar thresholds being 6 dB or more above monopolar thresholds. Bipolar and quadrupolar stimulation appear to have larger dynamic ranges than monopolar stimulation associated with a less rapid growth in response to saturation.

Response growth can be inferred from physiological and behavioral measures. Measures of neural spikes from individual neurons and the peak magnitudes of evoked potentials to electrical pulses provide an indication of response growth. For clinical measures the detection threshold, loudness estimates, comfort levels, and maximum tolerable levels can be estimated from patient responses.

Figure 3:
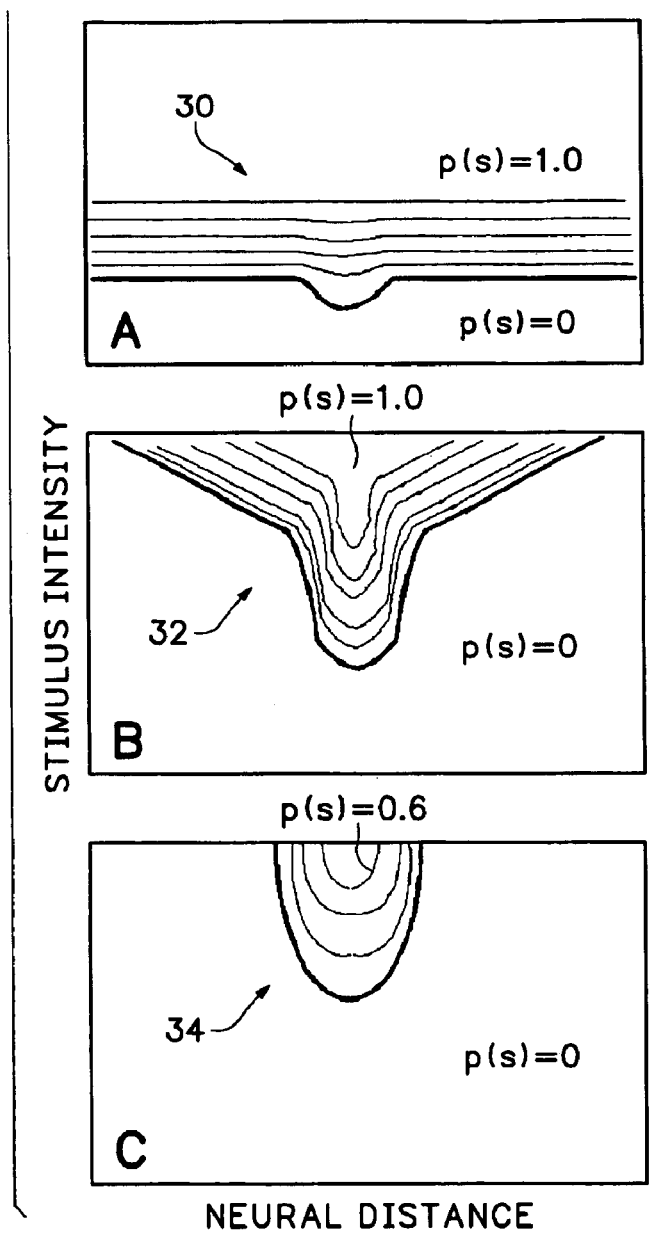
FIG. 3A is an illustration of the response areas of the cochlea for a low-threshold, minimally localized area.
FIG. 3B is an illustration of the response areas of the cochlea for a mid-threshold, medium localized area.
FIG. 3C is an illustration of the response areas of the cochlea for a high-threshold, spatially restricted response area.

Channel Independence and Minimizing Threshold. As with all information transmission, the number of independently variable information channels determines the potential number of alternatives that can be represented. The history of cochlear implants supports this dictum in that spatial and temporal resolution, in the form of more array contacts and higher pulse rates, appears correlated with better speech comprehension, that is, more information. Associating stimulation in one region of the cochlea with an information channel implies that achieving the maximum independence for its effect from stimulation at neighboring regions will enhance system performance. Low thresholds minimize the power needed to operate implantable stimulators, the size of the electrodes needed to support a given current or charge, and reduce the chance of producing harmful electrochemical byproducts and eroding electrode contacts. Monopolar stimulation produces low thresholds but great overlap in the neural regions activated, i.e., very poor channel independence, while high thresholds result from multipolar stimulation even though they have good channel independence. This is illustrated in FIG. 3 shown as the decreasing spatial spread of neural activity, measured as neural spike probability, in the transition from monopolar stimulation (panel A) to bipolar (panel B) and tripolar stimulation (panel C). The method to be described achieves the benefits of channel independence, characteristic of tripolar stimulation, and low thresholds, characteristic of monopolar stimulation.

The Method

Figure 4:
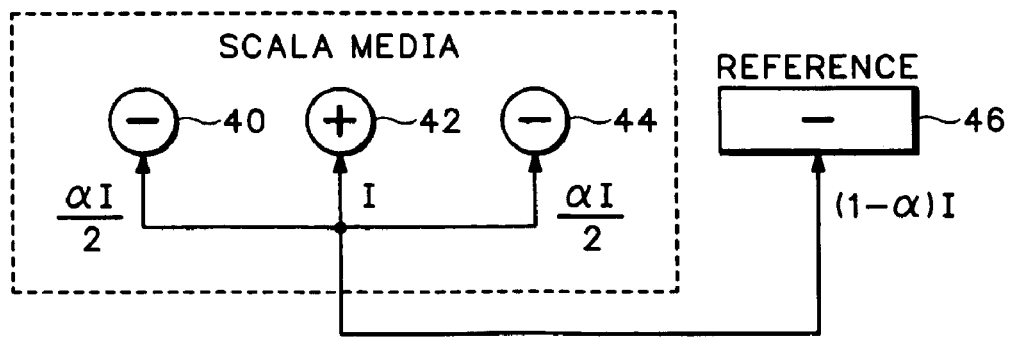
FIG. 4 is an illustration of a contact configuration used for quadrupole stimulation.

Curve sets 30 and 34 in FIG. 3 characterize the response areas for the neural population activated by electrical stimulation of the cochlea with monopolar and quadrupolar stimulation, respectively. The transition from A to C is from a low-threshold, minimally localized response area to a high-threshold, spatially restricted response area. The method partially outlined in FIG. 4 provides the means for a continuous transition from these conditions through the use of active contacts 40, 42 and 44 and passive reference contact 46.

Quadrupolar stimulation spatially restricts the response area because the active lateral contacts 40 constrain the field divergence, and thereby the local field gradients and stimulated neural population, to a small area near the active contacts 40. Controlling the current paths with monopolar stimulation (low-threshold, spatially extended response area) and quadrupolar stimulation (high-threshold, spatially restricted response) according to an intensity-dependent function will produce a low-threshold, spatially restricted response area. Current from the central scalar contact I is divided into monopolar current $I_m$ and quadrupolar current $I_q$ $$I = I_q + I_m$$

based on the variable $\alpha$ ($0 \leq \alpha \leq 1.0$) such that $$I = \alpha I + (1-\alpha)I$$

The quadrupolar current $$I_q = \alpha I = \frac{\alpha I}{2} + \frac{\alpha I}{2}$$

is the sum of current to the scalar contacts 40 and 44 adjacent to the central 42. The case of balanced currents for a quadrupole can be generalized to tripolar stimulation without the restriction of equal currents through the adjacent contacts.

Figure 5:
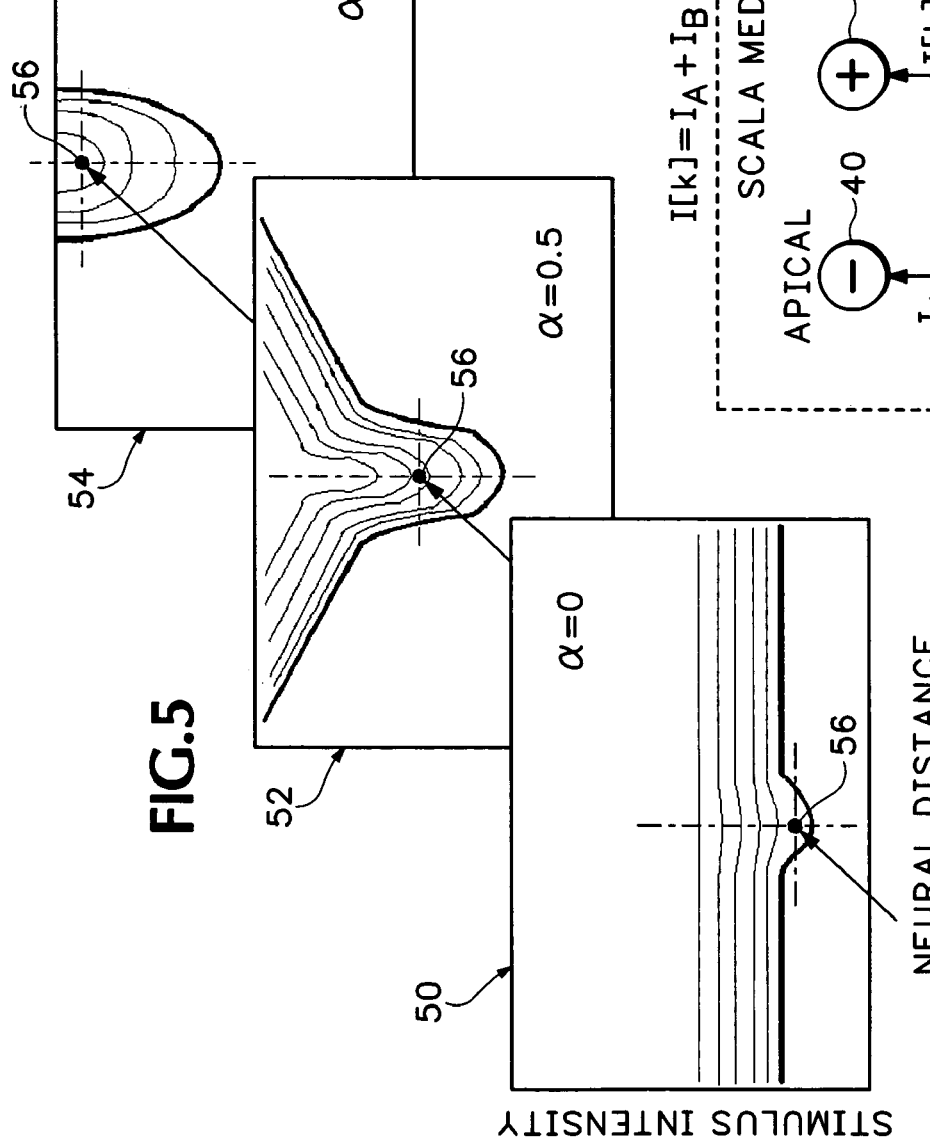
FIG. 5 is an illustration of the response areas of the cochlea for a low-threshold, minimally localized area, a mid-threshold, medium localized area, and a high-threshold, spatially restricted response area, also showing the cochlear stimulation perceived location.

The result of varying α is suggested for three curve sets 50, 52 and 54 in FIG. 5. The place of cochlear stimulation 56 remains the same, as does the site of activation in the neural population (vertical dashed lines). The extent of neural activation (horizontal dashed lines) would normally expand widely for low-threshold, monopolar stimulation (bottom panel), but using α to change to the quadrupolar stimulation mode restricts the spread of activation. Note that stimulus intensity and α vary together. It is necessary to define the nature and limits of the function relating α to the magnitude of sound determining the intensity of stimulus pulses.

The peak intensity for each electrical pulse is a function of a magnitude value $m_t$ in a series of discrete time-frequency-magnitude (TFM™) events indexed by t (described in referenced U.S. Pat. No. 6,480,820). Transforming the discrete time series $m_t$ to a series of pulse intensities $s_t$ is most directly based on two functions, one relating the loudness growth to electrical pulse intensity and the other electrical pulse intensity to sound magnitude. These two functions can be combined, and for discussion purposes a power function $$s_t = k m_t^p$$

will be assumed where k is a scaling constant and p is an exponent whose values are determined from clinical measures. Psychophysical measures are used to estimate the threshold and MCL for $s_t$ with corresponding values for $m_t$. Stimulation levels are restricted to be within these limits. The limits and function parameters must be estimated for each site of stimulation in the cochlea. The site of stimulation is mapped from instantaneous stimulus frequency $f_t$ and corresponds to the "central electrode contact" referred to here and will be indexed by i.

Implementation of the method requires that stimulus intensity be related to α so that the mapping $$s_t \to \alpha_t$$

must be determined. This mapping is one-to-one, monotonic, and limited by threshold and MCL on $s_t$. In summary, mappings are established for all stimulation sites indexed by i from instantaneous sound magnitude $m_t$ at time t to pulse intensity $s_t$ and the parameter α governing the stimulation mode:

$$m_t \xrightarrow{i} (s_t, \alpha_t)$$

In practice threshold and MCL would not be estimated on $s_t$ alone but on the full mapping function. Specifically threshold would be estimated with monopolar stimulation (α=0), and MCL would be estimated with quadrupolar stimulation (α=1.0). The form of the intervening map would meet the criteria of a smooth loudness growth and retention of channel independence over its range.

In generalizing to tripolar stimulation, three parameters represent how and where electrical current is passed for an elementary tripolar stimulation arrangement in cochlear implants:

1. the absolute current I[k] passed through a "central" electrode contact at position k along an array of contacts indexed from 1 to N.

2. the relative distribution of that current to adjacent, more apical (A) versus more basal (B) contacts to be represented by the parameter β defined below.
3. the relative distribution of that current to the adjacent contacts versus a distant return (or reference) contact (R) to be represented by the parameter α defined below.

Figure 6:
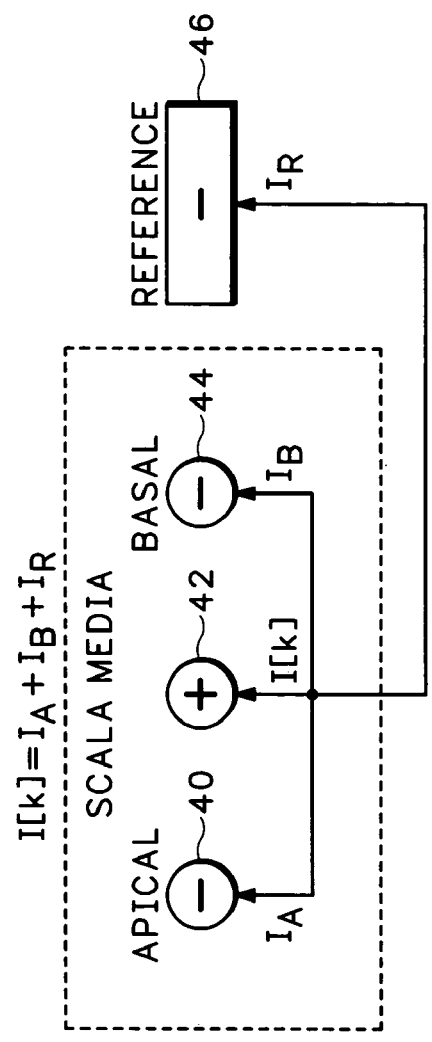
FIG. 6 is an illustration of a contact configuration used for steered stimulation.

The FIG. 6 shows the currents from contact 40 (IA), contact 42 (I[k]), contact 44 (IB), and contact 46 (IR) involved for one polarity. During a biphasic pulse the current directions would reverse to maintain charge balance over time, but this does not bear directly on the arguments. The steering parameter β determines the relative current distribution to the more apical and basal contacts, specifically, $$\beta = \frac{I_A - I_B}{I_A + I_B}$$

This parameter ranges from 1.0 ("hard apical steering") to −1.0 ("hard basalward"). It is not defined for the condition where no current is passed to the adjacent contacts ($I_A + I_B = 0$), the monopole condition where α=0 as described below. When β=0 the currents to the adjacent contacts are split evenly with $I_A = I_B$, and, assuming a homogeneous, isotropic tissue impedance, the field is concentrated symmetrically over the central contact. For β=1.0 current is passed only between the central and more apical contact shifting the field effect to its most apical position (excluding effects from α). The field is shifted most basalward when β=−1.0. If no current is passed to the return contact the β=1.0 and β=−1.0 conditions are dipole stimulations.

The total current is only indexed at the central contact as defined by the contact position along the array to avoid complexity in notation. All of the component currents $I_A$, $I_B$, and $I_R$ along with α and β are specific to cochlear position and can be position indexed. Multiple tripoles can coexist in an additive manner. While β specifies field steering, α is concerned with restriction of the field in a region near the central contact. Specifically, α determines the relative distribution of current between the adjacent contacts and the return contact as described previously. Using the notation introduced here:

$$I[k] = \alpha I[k] + (1-\alpha)I[k]$$
$$= \alpha I[k] + I[k] - (I_A + I_B)$$

leading to the definition $$\alpha = \frac{I_A + I_B}{I[k]} = \frac{I[k] - I_R}{I[k]}$$

a parameter ranging from 0.0 to 1.0 and representing the proportion of current in the tripole passing between the central contact and the adjacent contacts as opposed to the return contact. For α=0.0 no current passes to the adjacent contacts—the arrangement is a monopole. For α=1.0 all of the current passes to the adjacent contacts as generalized tripolar stimulation (β≠0), and for β=0 the arrangement is a quadrupole.

Figure 7:
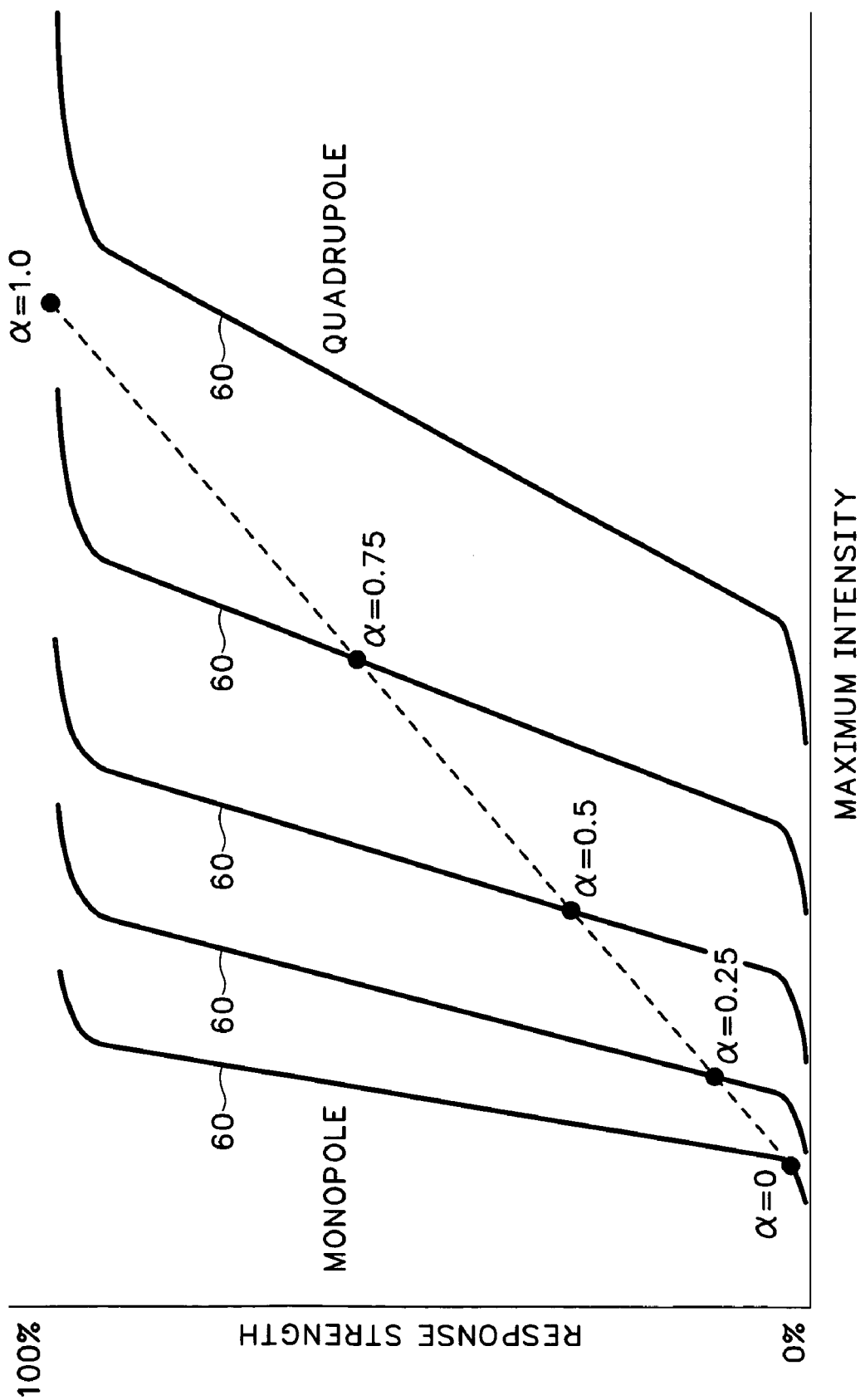
FIG. 7 is a graph showing response strength as a function of stimulus intensity for various values of $\alpha$.

While β provides a means for steering fields, manipulating the ratio α of current to adjacent and return electrodes affects dynamic range and field spread. FIG. 7 summarizes the effect of varying α on dynamic range.

Each curve 60 in FIG. 7 represents the growth of a response measure with stimulus intensity from threshold to a maximum or saturated response level. The response strength can be taken as the probability of a neural spike, the number of neural spikes, or a measure of loudness; observations exist for all of these. The technique is to achieve low threshold and a large dynamic range by varying α as a function of stimulus intensity achieving the function indicated with the dashed line. The vertical axis for the dashed line is an absolute measure of response strength, as opposed to the response strength range for a particular α.

Clinical adjustment procedures must match individual variations in loudness perceptions to functions involving α and β. The interaction of these parameters in determining loudness is likely and will necessitate adaptive estimation of the dynamic range for these parameters. A general adjustment procedure might involve the following steps, initially under the β=0 condition for each cochlear position:

1. Estimation of the monopolar threshold (α=0) for the central contact.
2. Increase stimulus intensity to estimate the monopolar MCL.
3. Adjust α from 0 upward with associated increases in stimulus intensity to approximate successive MCLs at higher α levels to estimate the MCL characterized by a stimulus current and $α_{max}$.
4. Establish the function between threshold with α=0 and MCL and $α_{max}$.
5. Determine if this function varies appreciably with changes in β.

In summary, α and β parameterize two useful manipulations of tripolar stimulation: morphing between a monopole and a quadrupole to gain low thresholds and increased dynamic range with a spatially narrow field, the method introduced here, and field steering from apical to basal directions to achieve potentially continuous spatial mapping in the vicinity of the central electrode. In practice stimulus intensity would be mapped into α and stimulus frequency into β. A two-dimensional parameter space is defined by α and β. They are mathematically independent, although this does not necessarily imply that their physiological effects are independent.

The preceding Detailed Description section is all to be taken by way of example, rather than limitation. In particular skilled persons will readily recognize that many of the concepts presented could find application either directly or by way of analogous concepts to the stimulation of muscle or brain or other nervous system tissue.

The invention claimed is:

1. A method of stimulating neurons in a patient's cochlea, comprising:
   (a) providing a plurality of cochlear electrodes, substantially arranged in a linear array within said cochlea;
   (b) providing a relatively distant electrode;
   (c) injecting a charge through a first one of said cochlear electrodes;
   (d) injecting an opposite charge on either:
      (i) said relatively distant electrode; or
      (ii) a set of adjacent cochlear electrodes, being adjacent to said first one of said cochlear electrodes; or
      (iii) on a combination of said relatively distant electrode and said set of adjacent electrodes; and
   (e) choosing said electrode or electrodes on which to inject charge in dependency on sound volume to be represented, lower volume sound causing more of said opposite charge to be injected through said relatively distant electrode and louder volume sounds causing more of said opposite charge to be injected through said adjacent electrodes.

2. The method of claim 1, wherein a scheme of cochlear stimulation is provided which provides a set of substantially optimal electrode configurations and charge amplitudes as a function of tone and loudness of prospectively represented sound, for minimizing current.

3. The method of claim 2 wherein said scheme of stimulation includes providing and using a look-up table.

4. The method of claim 1, wherein a scheme of cochlear stimulation is provided which provides a set of substantially optimal electrode configurations and charge amplitudes as a function of tone and loudness of prospectively represented sound, for minimizing charge.

5. The method of claim 1, wherein a scheme of cochlear stimulation is provided which provides a set of substantially optimal electrode configuration and charge amplitudes as a function of tone and loudness of prospectively represented sound, for minimizing energy drain over time.

6. The method of claim 1, wherein a scheme of cochlear stimulation is provided which provides a set of substantially optimal electrode configurations and charge amplitudes as a function of tone and loudness of prospectively represented sound for minimizing differences between said prospectively represented sound and sensing of said sound by said patient.

7. The method of claim 1, wherein said neurons have neuronal thresholds, said thresholds being a stimulation intensity below which said neurons do not respond and wherein stimulations only slightly above said neuronal thresholds are made by injecting said opposite charge on said relatively distant electrode but substantially no opposite charge on said set of adjacent electrodes.

8. The method of claim 1, wherein stimulations of from about 100 microamps to about 200 microamps are made by injecting said opposite charge on said relatively distant electrode but substantially no opposite charge on said set of adjacent electrodes.

9. The method of claim 1, wherein said neurons have a maximum stimulation level and wherein for stimulations near said maximum stimulation level, opposite charge is injected on said set of adjacent electrodes but substantially no opposite charge on said relatively distant electrode.

10. The method claim 1, wherein stimulations of from 1 milliamp to 2 milliamps are made by placing said opposite charge on said set of adjacent electrodes but substantially no opposite charge on said relatively distant electrode.

11. The method of claim 1, wherein said neurons have neuronal thresholds, said thresholds being a stimulation intensity below which said neurons do not respond and said neurons have a maximum stimulation level and wherein stimulation between slightly above said neuronal thresholds to maximum stimulation levels are made by injecting said opposite charge on both said relatively distant electrode and said set of adjacent electrodes.

12. The method of claim 1, wherein stimulation of from about 200 microamps to about 1 milliamp are made by placing said opposite charge on both said relatively distant electrode and said set of adjacent electrodes.

13. The method of claim 1, wherein said set of adjacent electrodes includes a single adjacent electrode.

14. The method of claim 1, wherein said set of adjacent electrodes includes a plurality of adjacent electrodes on either side of said first one of said cochlear electrodes.

15. A method of generating a scheme of cochlear stimulation adapted to translate volume and tone of sound received at a microphone associated to a patient's ear, to a stimulation of the cochlea of said ear, including determining stimulating current level to be applied through a stimulating electrode and the apportionment of return current levels through return electrodes, including a relatively distant electrode, said method comprising:

(a) compiling a data base of values, for a plurality of subject electrodes implanted along said cochlea, by:
  (i) using said subject electrode to stimulate said cochlea at a first electric polarity and placing an opposite current on said relatively distant electrode and determining a reaction or lack thereof to said stimulation;
  (ii) repeating step (i) until a minimum level of current necessary to said reaction is determined;
  (iii) recording said minimum level determined in step (ii);
  (iv) using said subject electrode to stimulate said cochlea at a first electric polarity and placing an opposite current on at least one adjacent cochlear electrode site; and
  (v) determining a maximum comfortable level of stimulation; and
  (vi) recording said maximum comfortable level of stimulation; and (b) assigning a function for prospective received sound values for choosing a stimulating electrode, determining stimulating current level and apportioning return electricity between a set of return electrodes in dependence on choice of stimulating electrode and prospective stimulating current level relative to said minimum and maximum levels determined in step (a).

16. The method of claim 15 wherein said minimum level of current necessary to create neural excitation is determined by asking said patient if said patient hears a sound.

17. The method of claim 15 wherein said minimum level of current necessary to create neural excitation is determined by sensing electric activity indicative of neural excitation subsequent to said stimulation.

18. The method of claim 15 wherein said maximum comfortable level of current necessary to create neural excitation is determined by questioning said patient.

19. The method of claim 15 wherein said maximum comfortable level of current necessary to create neural excitation is determined by sensing electric activity indicative of neural excitation subsequent to said stimulation.

* * * * *